US009737874B2

(12) United States Patent
Wattebled et al.

(10) Patent No.: US 9,737,874 B2
(45) Date of Patent: *Aug. 22, 2017

(54) WATER-ABSORBING POLYMER HAVING A HIGH ABSORPTION RATE

(75) Inventors: Laurent Wattebled, Dusseldorf (DE); Christoph Loick, Tonisvorst (DE); Jorg Harren, Baesweiler (DE); Stefan Leininger, Langenselbold (DE)

(73) Assignee: Evonik Degussa GmbH, Essen (DE)

( * ) Notice: Subject to any disclaimer, the term of this patent is extended or adjusted under 35 U.S.C. 154(b) by 155 days.

This patent is subject to a terminal disclaimer.

(21) Appl. No.: 14/110,579

(22) PCT Filed: Apr. 3, 2012

(86) PCT No.: PCT/EP2012/056019
§ 371 (c)(1),
(2), (4) Date: Nov. 6, 2013

(87) PCT Pub. No.: WO2012/143235
PCT Pub. Date: Oct. 26, 2012

(65) Prior Publication Data
US 2014/0054497 A1 Feb. 27, 2014

(30) Foreign Application Priority Data
Apr. 20, 2011 (DE) .................. 10 2011 007 723

(51) Int. Cl.
B01J 20/28 (2006.01)
B01J 20/30 (2006.01)
C08F 220/06 (2006.01)
A61L 15/42 (2006.01)
A61L 15/60 (2006.01)
C08F 2/16 (2006.01)
B01J 20/18 (2006.01)
B01J 20/20 (2006.01)
B01J 20/26 (2006.01)
C08J 3/12 (2006.01)
C08J 3/24 (2006.01)
B01J 20/04 (2006.01)
C08F 2/44 (2006.01)

(52) U.S. Cl.
CPC ....... B01J 20/28045 (2013.01); A61L 15/425 (2013.01); A61L 15/60 (2013.01); B01J 20/043 (2013.01); B01J 20/18 (2013.01); B01J 20/20 (2013.01); B01J 20/264 (2013.01); B01J 20/267 (2013.01); B01J 20/28004 (2013.01); B01J 20/28023 (2013.01); B01J 20/28028 (2013.01); B01J 20/28033 (2013.01); B01J 20/3014 (2013.01); B01J 20/3021 (2013.01); B01J 20/3028 (2013.01); C08F 2/16 (2013.01); C08F 220/06 (2013.01); C08J 3/12 (2013.01); C08J 3/24 (2013.01); B01J 2220/68 (2013.01); C08F 2/44 (2013.01); C08J 2333/00 (2013.01)

(58) Field of Classification Search
None
See application file for complete search history.

(56) References Cited

U.S. PATENT DOCUMENTS

| 4,076,663 | A | 2/1978 | Masuda et al. |
| 4,179,367 | A | 12/1979 | Barthell et al. |
| 4,286,082 | A | 8/1981 | Tsubakimoto et al. |
| 4,587,308 | A | 5/1986 | Makita et al. |
| 5,118,719 | A | 6/1992 | Lind |
| 5,399,591 | A | 3/1995 | Smith et al. |
| 5,409,771 | A | 4/1995 | Dahmen et al. |
| 5,462,972 | A | 10/1995 | Smith et al. |
| 5,610,220 | A | 3/1997 | Klimmek et al. |
| 5,672,633 | A | 9/1997 | Brehm et al. |
| 5,712,316 | A | 1/1998 | Dahmen et al. |
| 5,830,543 | A | 11/1998 | Miyake et al. |
| 5,985,944 | A | 11/1999 | Ishizaki et al. |
| 6,087,450 | A | 7/2000 | Breitbach et al. |
| 6,100,305 | A | 8/2000 | Miyake et al. |
| 6,143,821 | A | 11/2000 | Houben |
| 6,251,960 | B1 | 6/2001 | Ishizaki et al. |
| 6,399,668 | B1 | 6/2002 | Miyake et al. |
| 6,620,889 | B1 | 9/2003 | Mertens et al. |
| 6,831,142 | B2 | 12/2004 | Mertens et al. |
| 6,911,572 | B1 | 6/2005 | Bruhn et al. |

(Continued)

FOREIGN PATENT DOCUMENTS

| CN | 100345891 C | 10/2007 |
| CN | 100443125 C | 12/2008 |

(Continued)

OTHER PUBLICATIONS

Tronox Soda Ash Product Sheet.*

(Continued)

Primary Examiner — Tanisha Diggs
(74) Attorney, Agent, or Firm — Bernard Lau; Linda S. Li; Jason S. Ngui

(57) ABSTRACT

A process for producing a water-absorbing polymer composition, comprising the process steps of (i) mixing (α1) 0.1 to 99.999% by weight of ethylenically unsaturated monomers containing acid groups or salts thereof (α2) 0 to 70% by weight of polymerized, ethylenically unsaturated monomers copolymerizable with (α1), (α3) 0.001 to 10% by weight of one or more crosslinkers, (α4) 0 to 30% by weight of water-soluble polymers, and (α5) 0 to 20% by weight of one or more assistants, where the sum of their weights (α1) to (α5) is 100% by weight, (ii) free-radical polymerization with crosslinking to form a water-insoluble aqueous untreated hydrogel polymer, and surface postcrosslinking the ground hydrogel polymer wherein blowing agents having a particle size of 100 μm to 900 μm are added to the aqueous monomer solution prior to the addition of the initiator and the start of the free-radical polymerization.

7 Claims, No Drawings

(56) References Cited

U.S. PATENT DOCUMENTS

| | | | |
|---|---|---|---|
| 6,958,429 B2 | 10/2005 | Bruhn et al. | |
| 7,163,966 B2 | 1/2007 | Joy et al. | |
| 7,179,862 B2 | 2/2007 | Mertens et al. | |
| 7,285,599 B2 | 10/2007 | Mertens et al. | |
| 7,615,579 B2 | 11/2009 | Joy et al. | |
| 7,625,957 B2 | 12/2009 | Harren et al. | |
| 7,833,624 B2 | 11/2010 | Harren et al. | |
| 7,956,027 B2 | 6/2011 | Leininger et al. | |
| 8,048,942 B2 | 11/2011 | Fricker et al. | |
| 8,063,121 B2 | 11/2011 | Fricker et al. | |
| 8,198,385 B2 | 6/2012 | Gartner et al. | |
| 8,252,873 B1 | 8/2012 | Gartner et al. | |
| 8,349,913 B2 | 1/2013 | Harren et al. | |
| 8,357,766 B2 | 1/2013 | Fricker et al. | |
| 8,420,567 B1 | 4/2013 | Naumann et al. | |
| 8,445,596 B2 | 5/2013 | Mertens et al. | |
| 8,476,189 B1 | 7/2013 | Naumann et al. | |
| 2002/0115971 A1 | 8/2002 | Holmes et al. | |
| 2005/0137546 A1 | 6/2005 | Joy et al. | |
| 2009/0191408 A1* | 7/2009 | Tian | A61L 15/18 428/402 |
| 2010/0036004 A1 | 2/2010 | Harren et al. | |
| 2010/0099799 A1* | 4/2010 | Fricker | C08F 2/16 523/348 |
| 2010/0209379 A1 | 8/2010 | Furno et al. | |
| 2011/0009272 A1 | 1/2011 | Wattebled et al. | |
| 2011/0095227 A1 | 4/2011 | Herth et al. | |
| 2012/0001122 A1 | 1/2012 | Wattebled et al. | |
| 2012/0145956 A1 | 6/2012 | Walden et al. | |
| 2012/0302445 A1 | 11/2012 | Rudolph et al. | |
| 2012/0309905 A1 | 12/2012 | Fricker et al. | |

FOREIGN PATENT DOCUMENTS

| | | |
|---|---|---|
| DE | 2706135 A1 | 8/1978 |
| DE | 3503458 A1 | 8/1985 |
| DE | 4020780 C1 | 8/1991 |
| DE | 4323001 | 1/1993 |
| DE | 4244548 A1 | 7/1994 |
| DE | 4418818 A1 | 1/1995 |
| DE | 4333056 A1 | 3/1995 |
| DE | 19543366 A1 | 5/1997 |
| DE | 19543368 A1 | 5/1997 |
| DE | 19825486 A1 | 2/2000 |
| EP | 0443627 A2 | 8/1991 |
| EP | 0664207 A2 | 7/1995 |
| EP | 0744435 A1 | 11/1996 |
| JP | 08-47685 | 2/1996 |
| JP | 2007-514833 | 6/2007 |
| WO | 9526209 A1 | 10/1995 |
| WO | 9617884 A1 | 6/1996 |
| WO | 9934843 A1 | 7/1999 |
| WO | 02056812 A2 | 7/2002 |
| WO | 2005063313 A1 | 7/2005 |
| WO | 2008012181 A1 | 1/2008 |
| WO | 2009156229 A2 | 12/2009 |

OTHER PUBLICATIONS

German language International Search Report mailed on Jul. 26, 2012 in PCT/EP2012/056019, 3 pages.

German language Written Opinion mailed on Jul. 26, 2012 in PCT/EP2012/056019, 6 pages.

International Search Report mailed on Jul. 26, 2012 in PCT/EP2012/056019, 2 pages.

Loick et al., U.S. Appl. No. 13/876,736, filed Oct. 5, 2011.

Buchholz, Frederick L. and Graham, Andrew T., "Modern Superabsorbent Polymer Technology," copyright 1998, John Wiley & Sons, Inc., Chapter 1: "Absorbency and Superabsorbency," pp. 1-17 (19 pages).

Buchholz, Frederick L. and Graham, Andrew T., "Modern Superabsorbent Polymer Technology," copyright 1998, John Wiley & Sons, Inc., Chapter 2: "Chemistry of Superabsorbent Polyacrylates," pp. 19-67 (51 pages).

Buchholz, Frederick L. and Graham, Andrew T., "Modern Superabsorbent Polymer Technology," copyright 1998, John Wiley & Sons, Inc., Chapter 3: "Commercial Processes for the Manufacture of Superabsorbent Polymers," pp. 69-117 (51 pages).

Buchholz, Frederick L. and Graham, Andrew T., "Modern Superabsorbent Polymer Technology," copyright 1998, John Wiley & Sons, Inc., Chapter 4: "Analysis and Characterization of Superabsorbent Polymers," pp. 119-165 (49 pages).

Buchholz, Frederick L. and Graham, Andrew T., "Modern Superabsorbent Polymer Technology," copyright 1998, John Wiley & Sons, Inc., Chapter 5: "The Structure and Properties of Superabsorbent Polyacrylates," pp. 167-221 (57 pages).

* cited by examiner

WATER-ABSORBING POLYMER HAVING A HIGH ABSORPTION RATE

This application is a national stage application under 35 U.S.C. §371 of International Application No. PCT/EP2012/056019 filed 3 Apr. 2012, which claims priority to German Application No. DE 10 2011 007 723.5 filed 20 Apr. 2011, the disclosures of which are expressly incorporated herein by reference.

FIELD

The present invention relates to a process for producing water-absorbing polymers with high absorption rate, and to the use thereof.

BACKGROUND

The current trend in nappy construction is to produce even thinner constructions with reduced cellulose fibre content and increased superabsorbent content. The advantage of thinner constructions is exhibited not just in improved wear comfort but also in reduced costs in packaging and storage. With the trend toward ever thinner nappy constructions, the profile of requirements on the superabsorbents has changed significantly. Of crucial significance is now the ability of the hydrogel to conduct and distribute the liquid. Owing to the higher loading of the hygiene article (amount of superabsorbent per unit area), the polymer in the swollen state must not form a barrier layer for subsequent liquid (gel blocking). If the product has good transport properties, optimal exploitation of the overall hygiene article can be ensured.

In addition to the permeability of the superabsorbents (reported in the form of the "Saline Flow Conductivity—SFC") and the absorption capacity under compressive stress, the absorption rate of the superabsorbent particles in particular (reported in amount of liquid absorbed per gram of superabsorbent per second) is also a crucial criterion which enables statements about whether an absorbent core which comprises this superabsorbent in a large concentration and has only a low fluff content is capable, on its first contact with liquids, of absorbing them rapidly ("acquisition"). In the case of absorbent cores with a high superabsorbent content, this "acquisition" depends, among other factors, on the absorption rate of the superabsorbent material.

From the prior art, there are various known property rights which are supposed to enable an increase in the absorption. WO 96/17884A1 discloses a water-absorbing resin for which a solid blowing agent with a particle diameter of 1 to 100 μm is used in the monomer solution. In principle, preference is given to organic azo compounds and here specifically to the acrylic salts of azo compounds containing an amino group. Pure carbonates, ammonium nitride or mixtures thereof can optionally be used.

Disadvantages here are the rapid conversion of the azo compounds and the basic dispersion of the small solid particles in the monomer solution. Larger particles cannot be dispersed without separation of the different particles in the dispersion when left to stand. U.S. Pat. No. 5,118,719 discloses the addition of carbonate blowing agents in the form of carbonates, bicarbonates or mixtures thereof, or the introduction of gaseous carbon dioxide into the monomer solution. The blowing agent may be present in the dispersion in solid or dissolved form and is added shortly before or after the induction of the polymerization. This increases the absorption properties, such as a higher swell rate and gel stability. A disadvantage here is that the blowing agent has already escaped from the superabsorbent hydrogel before or during the gel formation, or forms larger bubbles which do not ensure a microporous structure of the superabsorbent polymer.

The general use of blowing agents is likewise described in publications EP 664207, U.S. Pat. Nos. 5,712,316, 5,399,591, 5,462,972. This likewise involves the use of usually inorganic blowing agents which release carbon dioxide in suspension, or gaseous or solid carbon dioxide which are added to the monomer solution. Predominantly potassium and ammonium compounds are used. An increase in the absorption and the absorption under pressure has been observed.

In general, it is an object of the present invention to overcome the disadvantages arising from the prior art.

More particularly, it is an object of the present invention to provide a process for producing a water-absorbing polymer that has an improved swell rate and faster absorption of liquids, while simultaneously maintaining the overall quality. This process should also be performable in a simple manner and not need the use of organic additives.

It is a particular object of the present invention to provide a process by which water-absorbing polymers can be produced, and a particularly high swell rate can be ensured.

It is a further object of the invention principally to specify a water-absorbing polymer, composites comprising such water-absorbing polymers and chemical products comprising such water-absorbing polymers or composites, said water-absorbing polymers having an increased absorption rate for aqueous solutions.

It is a further object of the present invention to provide a process for producing water-absorbing polymers, ensuring homogeneous distribution and very homogeneous action of the blowing agents in the reaction space.

These objects are achieved by the subject-matter of the category-forming claims. Advantageous configurations and developments which can occur individually or in combination form the subject-matter of the dependent claims in each case.

SUMMARY

The present invention includes carious embodiments as set forth herein. In particular, the present invention is directed to a process for producing a water-absorbing polymer composition, comprising the process steps of
  (i) mixing
    ($\alpha$1) from 0.1 to 99.999% by weight of polymerizable, ethylenically unsaturated monomers containing acid groups or salts thereof or polymerizable, ethylenically unsaturated monomers including a protonated or quaternized nitrogen, or mixtures thereof, particular preference being given to mixtures including at least ethylenically unsaturated monomers containing acid groups, preferably acrylic acid,
    ($\alpha$2) from 0 to 70% by weight of polymerizable, ethylenically unsaturated monomers copolymerizable with ($\alpha$1),
    ($\alpha$3) from 0.001 to 10% by weight of one or more crosslinkers,
    ($\alpha$4) from 0 to 30% by weight of water-soluble polymers, and
    ($\alpha$5) from 0 to 20% by weight of one or more assistants, where the sum of their weights ($\alpha$1) to ($\alpha$5) is 100% by weight,
  (ii) free-radical polymerization with crosslinking to form a water-insoluble aqueous untreated hydrogel polymer, (iii) drying the hydro polymer,
(iv) optionally grinding and sieving the water-absorbing polymer,
(v) surface postcrosslinking the ground hydrogel polymer and
(vi) drying and finishing the water-absorbing polymer, wherein
blowing agents having a particle size of 100 μm to 900 μm are added to the aqueous monomer solution prior to the addition of the initiator and the start of the free-radical polymerization.

DETAILED DESCRIPTION

A contribution to the achievement of the object stated at the outset is made by the process for producing a water-absorbing polymer composition, comprising the process steps of
(i) mixing
(α1) 0.1 to 99.999% by weight, preferably 20 to 98.99% by weight and more preferably 30 to 98.95% by weight of polymerizable, ethylenically unsaturated monomers containing acid groups or salts thereof or polymerizable, ethylenically unsaturated monomers including a protonated or quaternized nitrogen, or mixtures thereof, particular preference being given to mixtures including at least ethylenically unsaturated monomers containing acid groups, preferably acrylic acid,
(α2) 0 to 70% by weight, preferably 1 to 60% by weight and more preferably 1 to 40% by weight of polymerized, ethylenically unsaturated monomers copolymerizable with (α1),
(α3) 0.001 to 10% by weight, preferably 0.01 to 7% by weight and more preferably 0.05 to 5% by weight of one or more crosslinkers,
(α4) 0 to 30% by weight, preferably 1 to 20% by weight and more preferably 5 to 10% by weight of water-soluble polymers, and
(α5) 0 to 20% by weight, preferably 0.01 to 7% by weight and more preferably 0.05 to 5% by weight of one or more assistants, where the sum of their weights (α1) to (α5) is 100% by weight,
(ii) free-radical polymerization with crosslinking to form a water-insoluble aqueous untreated hydrogel polymer,
(iii) drying the hydrogel polymer,
(iv) optionally grinding and sieving the water-absorbing polymer,
(v) surface postcrosslinking the ground hydrogel polymer and
(vi) drying and finishing the water-absorbing polymer, wherein
blowing agents having a particle size of 100 μm to 900 μm are added to the aqueous monomer solution prior to the addition of the initiator and the start of the free-radical polymerization.

In a further embodiment of the present invention, in step iii), the comminution can optionally additionally be effected prior to the drying of the hydrogel polymer.

The blowing agents used may be all carbonates from the group of lithium carbonate, sodium carbonate, potassium carbonate, rubidium carbonate, caesium carbonate, or higher-valency metal ions such as beryllium carbonate, calcium carbonate, magnesium carbonate, strontium carbonate or mixtures thereof Further compounds used may also be granulated carbonates, which are produced as mixed salts of a carbonate and/or percarbonate with a further salt which functions as an outer layer, for example a sulphate compound.

The sodium carbonate used for the process according to the invention can be prepared, for example, as described in WO 2008/012181. This is a sodium carbonate which has a particulate structure which consists of several layers of sodium carbonate and sodium sulphate and/or a high-temperature phase composed of a double salt of $Na_4(SO_4)_{1+n}(CO_3)_{1-n}$ where n is from 0 to 0.5. This carbonate compound has a particle size distribution in the range from 100 to 900 μm. The production is effected by means of fluidized bed buildup granulation. This compound is used as a cleaning agent in machine dishwashers. In the process according to the invention, preference is given to using pure granulated sodium carbonate according to WO 2008/012181.

Preference is given to a particle size of 200 μm to 800 μm and particular preference to a particle size in the range from 300 μm to 700 μm. The particles may have amorphous or regular three-dimensional configuration.

In a further embodiment, the blowing agent used may comprise, for example, amorphous particles having a particle size of 200 μm to 800 μm, preferably 300 μm to 700 μm and more preferably 400 μm to 600 μm.

According to the invention, steps i) and ii) of the process according to the invention are executed in a kneading reactor. According to the invention, a kneading reactor which executes at least a corotating shaft movement is used here. Preference is given to using kneading reactors having at least two shafts.

Advantageously, the use of the granules as the blowing agent and a kneader with at least one shaft ensures homogeneous distribution of the blowing agent in the resulting hydrogel. The removal layer by layer is caused by intensive kneading processes and the energy dissipation, which is ideal for these purposes, in the reaction interior of the kneader. This additionally enables the homogeneous release of the carbon dioxide in the course of the reaction. As a result, a water-absorbing polymer having a higher swell rate is advantageously obtained.

Surprisingly, the positive effects on the swell rate are observed with the granulated blowing agent only in combination with the kneader polymerization process. The use of this above-described granulated carbonate composition provided with a layer structure for production of the superabsorbent in poly belt technology does not lead to any significant effect on the swell rate (FSR).

It is a particular object of the present invention to provide a process by which absorbent polymers can be produced, and a particularly high swell rate can be ensured.

It is a further object of the present invention to provide a process for producing water-absorbent polymer which enable a homogeneous distribution of the soda particles.

This object is achieved by the process according to the invention in which process steps i) and ii) take place in a kneading reactor having at least one shaft.

The removal layer by layer is caused by intensive kneading processes and the homogeneous energy dissipation, which is ideal for these purposes, in the reaction interior.

Surprisingly, the kneading reactor in batchwise or continuous operation with an at least one-shaft system shows that granulated sodium carbonate is incorporated homogeneously in the monomer solution and process step ii) at a speed of 10 to 80 revolutions per min. The process step is preferably affected at rotation rates of the kneading reactor of 15 to 60 revolutions per min. and more preferably at 20 to 35 revolutions per min.

Surprisingly, the process according to the invention produced water-absorbing polymers which have an FSR in the range from 0.3 to 0.55, preferably 0.35 to 0.45.

In the case of use of granulated soda, it has been found, surprisingly, that the inventive effect led at a particular time, after the addition of hydrogen peroxide and before ascorbic acid addition to the monomer solution in the kneading reactor, to higher swell rates of the resultant superabsorbent polymer, without any adverse effect on the other characteristics of the water-absorbing polymer. This effect is not observed in any case with the static poly belt process. The use of sodium carbonate of different density (light density and heavy density) likewise led to an increased swell rate value, but the rise in the swell rate in the case of the kneading process is not as marked as that resulting from the addition of the granulated sodium carbonate. In addition, the use of sodium carbonate allows porosity, such that an increase in the particle surface area is enabled.

Preferably, the combination of the sodium carbonate and the one corotatory twin-shaft kneader in steps i) and ii) of the process according to the invention lowers the oxygen, greatly minimizes the destruction of the granules, and ensures incorporation of the carbonate and also homogeneous release of carbon dioxide.

The monoethylenically unsaturated monomers ($\alpha 1$) containing acid groups may be partly or fully, preferably partly, neutralized. The monoethylenically unsaturated monomers containing acid groups are preferably neutralized to an extent of at least 10 mol %, more preferably to an extent of at least 25 to 50 mol % and further preferably to an extent of 50 to 90 mol %. The neutralization of the monomers ($\alpha 1$) may precede else follow the polymerization. In this case, the partial neutralization is effected to an extent of at least 10 mol %, more preferably to an extent of at least 25 to 50 mol % and further preferably to an extent of 50 to 90 mol % neutralized. In addition, neutralization can be effected with alkali metal hydroxides, alkaline earth metal hydroxides, ammonia, and carbonates and bicarbonates. In addition, any further base which forms a water-soluble salt with the acid is conceivable. Mixed neutralization with different bases is also conceivable. Preference is given to neutralization with ammonia or with alkali metal hydroxides, more preferably with sodium hydroxide or with ammonia.

In addition, the free acid groups in a polymer may predominate, such that this polymer has a pH within the acidic range. This acidic water-absorbing polymer may be at least partly neutralized by a polymer with free basic groups, preferably amine groups, which is basic compared to the acid polymer. These polymers are referred to in the literature as "Mixed-Bed Ion-Exchange Absorbent Polymers" (MBIEA polymers) and are disclosed inter alia in WO 99/34843. The disclosure of WO 99/34843 is hereby incorporated by reference and is therefore considered to form part of the disclosure. In general, MBIEA polymers constitute a composition which includes firstly basic polymers capable of exchanging anions, and secondly a polymer which is acidic compared to the basic polymer and is capable of exchanging cations. The basic polymer has basic groups and is typically obtained by the polymerization of monomers which bear basic groups or groups which can be converted to basic groups. These monomers are in particular those which have primary, secondary or tertiary amines or the corresponding phosphines, or at least two of the above functional groups. This group of monomers includes especially ethyleneamine, allylamine, diallylamine, 4-aminobutene, alkyloxycyclines, vinylformamide, 5-aminopentene, carbodiimide, formaldacine, melamine and the like, and the secondary or tertiary amine derivatives thereof Preferred monoethylenically unsaturated monomers ($\alpha 1$) containing acid groups are acrylic acid, methacrylic acid, ethacrylic acid, $\alpha$-chloroacrylic acid, $\alpha$-cyanoacrylic acid, $\beta$-methylacrylic acid (crotonic acid), $\alpha$-phenylacrylic acid, $\beta$-acryloyloxypropionoic acid, sorbic acid, $\alpha$-chlorosorbic acid, 2'-methylisocrotonic acid, cinnamic acid, p-chlorocinnamic acid, $\beta$-stearyl acid, itaconic acid, citraconic acid, mesaconic acid, glutaconic acid, aconitic acid, maleic acid, fumaric acid, tricarboxyethylene and maleic anhydride, preference being given particularly to acrylic acid and methacrylic acid and additionally to acrylic acid.

In addition to these monomers containing carboxylate groups, preferred monoethylenically unsaturated monomers ($\alpha 1$) containing acid groups additionally include ethylenically unsaturated sulphonic acid monomers or ethylenically unsaturated phosphonic acid monomers.

Preferred ethylenically unsaturated sulphonic acid monomers are allylsulphonic acid or aliphatic or aromatic vinylsulphonic acids or acrylic or methacrylic sulphonic acids. Preferred aliphatic or aromatic vinylsulphonic acids are vinylsulphonic acid, 4-vinylbenzylsulphonic acid, vinyltoluenesulphonic acid and styrenesulphonic acid. Preferred acryloyl- or methacryloylsulphonic acids are sulphoethyl (meth)acrylate, sulphopropyl (meth)acrylate, 2-hydroxy-3-methacryloyloxypropylsulphonic acid, and (meth)acrylamidoalkylsulphonic acids such as 2-acrylamido-2-methylpropanesulphonic acid.

Preferred ethylenically unsaturated phosphonic acid monomers are vinylphosphonic acid, allylphosphonic acid, vinylbenzylphosphonic acid, (meth)acrylamidoalkylphosphonic acids, acrylamidoalkyldiphosphonic acids, phosphonomethylated vinylamines and (meth)acryloylphosphonic acid derivatives.

Preferred ethylenically unsaturated monomers ($\alpha 1$) containing a protonated nitrogen are preferably dialkylaminoalkyl (meth)acrylates in protonated form, for example dimethylaminoethyl (meth)acrylate hydrochloride or dimethylaminoethyl (meth)acrylate hydrosulphate, and dialkylaminoalkyl(meth)acrylamides in protonated form, for example dimethylaminoethyl(meth)acrylamide hydrochloride, dimethylaminopropyl(meth)acrylamide hydrochloride, dimethylaminopropyl(meth)acrylamide hydrosulphate or dimethylaminoethyl(meth)acrylamide hydrosulphate.

Preferred ethylenically unsaturated monomers ($\alpha 1$) containing a quaternized nitrogen are dialkylammonioalkyl (meth)acrylates in quaternized form, for example trimethylammonioethyl (meth)acrylate methosulphate or dimethylethylammonioethyl (meth)acrylate ethosulphate, and (meth)acrylamidoalkyldialkylamines in quaternized form, for example (meth)acrylamidopropyltrimethylammonium chloride, trimethylammonioethyl (meth)acrylate chloride or (meth)acrylamidopropyltrimethylammonium sulphate.

Preferred monoethylenically unsaturated monomers ($\alpha 2$) copolymerizable with ($\alpha 1$) are acrylamides and methacrylamides.

Preferred (meth)acrylamides are, in addition to acrylamide and methacrylamide, alkyl-substituted (meth)acrylamides or aminoalkyl-substituted derivatives of (meth)acrylamide, such as N-methylol(meth)acrylamide, N,N-dimethylamino(meth)acrylamide, dimethyl(meth) acrylamide or diethyl(meth)acrylamide. Possible vinylamides are, for example, N-vinylamides, N-vinylformamides, N-vinylacetamides, N-vinyl-N-methylacetamides, N-vinyl-N-methylformamides, vinylpyrrolidone. Among these monomers, particular preference is given to acrylamide.

Additionally preferred as monoethylenically unsaturated monomers (α2) copolymerizable with (α1) are water-dispersible monomers. Preferred water-dispersible monomers are acrylic esters and methacrylic esters, such as methyl (meth)acrylate, ethyl (meth)acrylate, propyl (meth)acrylate or butyl (meth)acrylate, and also vinyl acetate, styrene and isobutylene.

Crosslinkers (α3) preferred in accordance with the invention are compounds having at least two ethylenically unsaturated groups within one molecule (crosslinker class I), compounds having at least two functional groups which can react with functional groups of monomers (α1) or (α2) in a condensation reaction (=condensation crosslinkers), in an addition reaction or in a ring-opening reaction (crosslinker class II), compounds which have at least one ethylenically unsaturated group and at least one functional group which can react with functional groups of monomers (α1) or (α2) in a condensation reaction, in an addition reaction or in a ring-opening reaction (crosslinker class III), or polyvalent metal cations (crosslinker class IV). The compounds of crosslinker class I achieve crosslinking of the polymers through the free-radical polymerization of the ethylenically unsaturated groups of the crosslinker molecule with the monoethylenically unsaturated monomers (α1) or (α2), while the compounds of the crosslinker class II and the polyvalent metal cations of crosslinker class IV achieve crosslinking of the polymers by a condensation reaction of the functional groups (crosslinker class II) or by electrostatic interaction of the polyvalent metal cation (crosslinker class IV) with the functional groups of monomers (α1) or (α2). In the case of the compounds of crosslinker class III, there is correspondingly crosslinking of the polymer both by free-radical polymerization of the ethylenically unsaturated group and by a condensation reaction between the functional group of the crosslinker and the functional groups of monomers (α1) or (α2).

Preferred compounds of crosslinker class I are poly(meth) acrylic esters which are obtained, for example, by the reaction of a polyol, for example ethylene glycol, propylene glycol, trimethylolpropane, 1,6-hexanediol, glycerol, pentaerythritol, polyethylene glycol or polypropylene glycol, of an amino alcohol, of a polyalkylenepolyamine, for example diethylenetriamine or triethylenetetramine, or of an alkoxylated polyol with acrylic acid or methacrylic acid. Preferred compounds of crosslinker class I are additionally polyvinyl compounds, poly(meth)allyl compounds, (meth)acrylic esters of a monovinyl compound or (meth)acrylic esters of a mono(meth)allyl compound, preferably of the mono(meth) allyl compounds of a polyol or of an amino alcohol. In this context, reference is made to DE 195 43 366 and DE 195 43 368. The disclosures are hereby incorporated by reference and therefore form part of the disclosure.

Examples of compounds of crosslinker class I include alkenyl di(meth)acrylates, for example ethylene glycol di(meth)acrylate, 1,3-propylene glycol di(meth)acrylate, 1,4-butylene glycol di(meth)acrylate, 1,3-butylene glycol di(meth)acrylate, 1,6-hexanediol di(meth)acrylate, 1,10-decanediol di(meth)acrylate, 1,12-dodecanediol di(meth)acrylate, 1,18-octadecanediol di(meth)acrylate, cyclopentanediol di(meth)acrylate, neopentyl glycol di(meth) acrylate, methylene di(meth)acrylate or pentaerythritol di(meth)acrylate, alkenyldi(meth)acrylamides, for example N-methyldi(meth)acrylamide, N,N'-3-methylbutylidenebis (meth)acrylamide, N,N'-(1,2-dihydroxyethylene)bis(meth) acrylamide, N,N'-hexamethylenebis(meth)acrylacryl-amide or N,N'-methylenebis(meth)acrylamide, polyalkoxy di(meth)acrylates, for example diethylene glycol di(meth)acrylate, triethylene glycol di(meth)acrylate, tetraethylene glycol di(meth)acrylate, dipropylene glycol di(meth)acrylate, tripropylene glycol di(meth)acrylate or tetrapropylene glycol di(meth)acrylate, bisphenol A di(meth)acrylate, ethoxylated bisphenol A di(meth)acrylate, benzylidene di(meth) acrylate, 1,3-di(meth)acryloyloxy-2-propanol, hydroquinone di(meth)acrylate, di(meth)acrylate esters of trimethylolpropane which has preferably been alkoxylated, preferably ethoxylated, with 1 to 30 mol of alkylene oxide per hydroxyl group, thioethylene glycol di(meth)acrylate, thiopropylene glycol di(meth)acrylate, thiopolyethylene glycol di(meth)acrylate, thiopolypropylene glycol di(meth) acrylate, divinyl ethers, for example 1,4-butanediol divinyl ether, divinyl esters, for example divinyl adipate, alkadienes, for example butadiene or 1,6-hexadiene, divinylbenzene, di(meth)allyl compounds, for example di(meth)allyl phthalate or di(meth)allyl succinate, homo- and copolymers of di(meth)allyldimethylammonium chloride and homo- and copolymers of diethyl(meth)allylammoniomethyl (meth) acrylate ammonium chloride, vinyl (meth)acryloyl compounds, for example vinyl (meth)acrylate, (meth)allyl (meth)acryloyl compounds, for example (meth)allyl (meth) acrylate, (meth)allyl (meth)acrylate ethoxylated with 1 to 30 mol of ethylene oxide per hydroxyl group, di(meth)allyl esters of polycarboxylic acids, for example di(meth)allyl maleate, di(meth)allyl fumarate, di(meth)allyl succinate or di(meth)allyl terephthalate, compounds having 3 or more ethylenically unsaturated, free-radically polymerizable groups, for example glyceryl tri(meth)acrylate, (meth)acrylate esters of glycerol which has been ethoxylated with preferably 1 to 30 mol of ethylene oxide per hydroxyl group, trimethylolpropane tri(meth)acrylate, tri(meth)acrylate esters of trimethylolpropane which has preferably been alkoxylated, preferably ethoxylated, with 1 to 30 mol of alkylene oxide per hydroxyl group, trimethacrylamide, (meth)allylidene di(meth)acrylate, 3-allyloxy-1,2-propanediol di(meth)acrylate, tri(meth)allyl cyanurate, tri(meth)allyl isocyanurate, pentaerythritol tetra(meth)acrylate, pentaerythritol tri(meth)acrylate, (meth)acrylic esters of pentaerythritol ethoxylated with preferably 1 to 30 mol of ethylene oxide per hydroxyl group, tris(2-hydroxyethyl) isocyanurate tri(meth)acrylate, trivinyl trimellitate, tri(meth) allylamine, di(meth)allylalkylamines, for example di(meth) allylmethylamine, tri(meth)allyl phosphate, tetra(meth)allylethylenediamine, poly(meth)allyl esters, tetra(meth) allyloxyethane or tetra(meth)allylammonium halides.

Preferred compounds of crosslinker class II are compounds which have at least two functional groups which can react in a condensation reaction (=condensation crosslinkers), in an addition reaction or in a ring-opening reaction with the functional groups of monomers (α1) or (α2), preferably with acid groups of monomers (α1). These functional groups of the compounds of crosslinker class II are preferably alcohol, amine, aldehyde, glycidyl, isocyanate, carbonate or epichloro functions.

Examples of compounds of crosslinker class II include polyols, for example ethylene glycol, polyethylene glycols such as diethylene glycol, triethylene glycol and tetraethylene glycol, propylene glycol, polypropylene glycols such as dipropylene glycol, tripropylene glycol or tetrapropylene glycol, 1,3-butanediol, 1,4-butanediol, 1,5-pentanediol, 2,4-pentanediol, 1,6-hexanediol, 2,5-hexanediol, glycerol, polyglycerol, trimethylolpropane, polyoxypropylene, oxyethylene-oxypropylene block copolymers, sorbitan fatty acid esters, polyoxyethylene sorbitan fatty acid esters, pentaerythritol, polyvinyl alcohol and sorbitol, amino alcohols, for example ethanolamine, diethanolamine, triethanolamine or propanolamine, polyamine compounds, for example ethylenediamine, diethylenetriamine, triethylenetetramine, tetraethylenepentamine or pentaethylenehexamine, polyglycidyl ether compounds such as ethylene glycol diglycidyl ether, polyethylene glycol diglycidyl ether, glyceryl diglycidyl ether, glyceryl polyglycidyl ether, pentaerythrityl polyglycidyl ether, propylene glycol diglycidyl ether, polypropylene glycol diglycidyl ether, neopentyl glycol diglycidyl ether, hexanediol glycidyl ether, trimethylolpropane polyglycidyl ether, sorbitol polyglycidyl ether, diglycidyl phthalate, adipic acid diglycidyl ether, 1,4-phenylenebis(2-oxazoline), glycidol, polyisocyanates, preferably diisocyanates such as toluene 2,4-diisocyanate and hexamethylene diisocyanate, polyaziridine compounds such as 2,2-bishydroxymethylbutanol tris [3-(1-aziridinyl)propionate], 1,6-hexamethylenediethyleneurea and diphenylmethanebis-4,4'-N,N'-diethyleneurea, halogen peroxides, for example epichloro- and epibromohydrin and α-methylepichlorohydrin, alkylene carbonates such as 1,3-dioxolan-2-one (ethylene carbonate), 4-methyl-1,3-dioxolan-2-one (propylene carbonate), 4,5-di-methyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one, 1,3-dioxolan-2-one, poly-1,3-dioxolan-2-one, polyquaternary amines such as condensation products of dimethylamines and epichlorohydrin. Preferred compounds of crosslinker class II are additionally polyoxazolines such as 1,2-ethylenebisoxazoline, crosslinkers with silane groups, such as y-glycidoxypropyltrimethoxysilane and y-aminopropyltrimethoxysilane, oxazolidinones such as 2-oxazolidinone, bis- and poly-2-oxazolidinones and diglycol silicates.

Preferred compounds of class III include hydroxyl- or amino-containing esters of (meth)acrylic acid, for example 2-hydroxyethyl (meth)acrylate and 2-hydroxypropyl (meth) acrylate, and also hydroxyl- or amino-containing (meth) acrylamides or mono(meth)allyl compounds of diols.

The polyvalent metal cations of crosslinker class IV derive preferably from mono- or polyvalent cations, the monovalent especially from alkali metals such as potassium, sodium, lithium, preference being given to lithium. Preferred divalent cations derive from zinc, beryllium, alkaline earth metals such as magnesium, calcium, strontium, preference being given to magnesium. Further higher-valency cations useable in accordance with the invention are cations of aluminium, iron, chromium, manganese, titanium, zirconium and other transition metals, and also double salts of such cations or mixtures of the salts mentioned.

Preference is given to using aluminium salts and alums and the different hydrates thereof, for example $AlCl_3 \times 6H_2O$, $NaAl(SO_4)_2 \times 12\ H_2O$, $KAl(SO_4)_2 12\ H_2O$ or $Al_2(SO_4)_3 \times 14\text{-}18\ H_2O$. Particular preference is given to using $Al_2(SO_4)_3$ and hydrates thereof as crosslinkers of crosslinking class IV.

The superabsorbent particles used in the process according to the invention are preferably crosslinked by crosslinkers of the following crosslinker classes, or by crosslinkers of the following combinations of crosslinker classes: I, II, III, IV, I II, I III, I IV, I II III, I II IV, I III IV, II III IV, II IV or III IV. The above combinations of crosslinker classes are each a preferred embodiments of crosslinkers of a superabsorbent particle used in the process according to the invention.

Further preferred embodiments of the superabsorbent particles used in the process according to the invention are polymers which are crosslinked by any of the aforementioned crosslinkers of crosslinker classes I. Among these, preference is given to water-soluble crosslinkers. In this context, particular preference is given to N,N'-methylenebisacrylamide, polyethylene glycol di(meth)acrylates, triallylmethylammonium chloride, tetraallylammonium chloride, and allyl nonaethylene glycol acrylate prepared with 9 mol of ethylene oxide per mole of acrylic acid.

The water-soluble polymers (α4) present in the superabsorbent particles may be water-soluble polymers, such as partly or fully hydrolysed polyvinyl alcohol, polyvinylpyrrolidone, starch or starch derivatives, polyglycols or polyacrylic acid, preferably incorporated in polymerized form. The molecular weight of these polymers is uncritical provided that they are water-soluble. Preferred water-soluble polymers are starch or starch derivatives or polyvinyl alcohol. The water-soluble polymers, preferably synthetic water-soluble polymers such as polyvinyl alcohol, can also serve as a graft base for the monomers to be polymerized.

The assistants (α5) present in the polymers are organic or inorganic particles, for example odour binders, especially zeolites or cyclodextrins, skincare substances, surfactants or antioxidants.

The preferred organic assistants include cyclodextrins or derivatives thereof, and polysaccharides. Also preferred are cellulose and cellulose derivatives such as CMC, cellulose ethers. Preferred cyclodextrins or cyclodextrin derivatives are those compounds disclosed in DE-A-198 25 486 at page 3 line 51 to page 4 line 61. The aforementioned section of this published patent application is hereby incorporated by reference and is considered to form part of the disclosure of the present invention. Particularly preferred cyclodextrins are underivatized α-, β-, γ- or δ-cyclodextrins.

The inorganic particulate assistants used may be any materials which are typically used to modify the properties of water-absorbing polymers. The preferred inorganic assistants include sulphates such as $Na_2SO_4$, lactates, for instance sodium lactate, silicates, especially framework silicates such as zeolites, or silicates which have been obtained by drying aqueous silica solutions or silica sols, for example the commercially available products such as precipitated silicas and fumed silicas, for example Aerosils having a particle size in the range from 5 to 50 nm, preferably in the range from 8 to 20 nm, such as "Aerosil 200" from Evonik Industries AG, aluminates, titanium dioxides, zinc oxides, clay materials, and further minerals familiar to those skilled in the art, and also carbonaceous inorganic materials.

Preferred silicates are all natural or synthetic silicates which are disclosed as silicates in Hollemann and Wiberg, Lehrbuch der Anorganischen Chemie [Inorganic Chemistry], Walter de Gruyter-Verlag, $91^{st}$-$100^{th}$ edition, 1985, on pages 750 to 783. The aforementioned section of this textbook is hereby incorporated by reference and is considered to form part of the disclosure of the present invention.

Particularly preferred silicates are the zeolites. The zeolites used may be all synthetic or natural zeolites known to those skilled in the art. Preferred natural zeolites are zeolites from the natrolite group, the harmotone group, the mordenite group, the chabasite group, the faujasite group (sodalite group) or the analcite group. Examples of natural zeolites are analcime, leucite, pollucite, wairakite, bellbergite, bikitaite, boggsite, brewsterite, chabasite, willhendersonite, cowlesite, dachiardite, edingtonite, epistilbite, erionite, faujasite, ferrierite, amicite, garronite, gismondine, gobbinsite, gmelinite, gonnardite, goosecreekite, harmotone, phillipsite, wellsite, clinoptilolite, heulandite, laumontite, levyne, mazzite, merlinoite, montesommaite, mordenite, mesolite, natrolite, scolecite, offretite, paranatrolite, paulingite, perlialite, barrerite, stilbite, stellerite, thomsonite, tschernichite or yugawaralite. Preferred synthetic zeolites are zeolite A, zeolite X, zeolite Y, zeolite P, or the product ABSCENTS.

The zeolites used may be zeolites of the so-called "intermediate" type, in which the $SiO_2/AlO_2$ ratio is less than 10; the $SiO_2/AlO_2$ ratio of these zeolites is more preferably within a range from 2 to 10. In addition to these "intermediate" zeolites, it is also possible to use zeolites of the "high" type, which include, for example, the known "molecular sieve" zeolites of the ZSM type, and β-zeolite. These "high" zeolites are preferably characterized by an $SiO_2/AlO_2$ ratio of at least 35, more preferably by an $SiO_2/AlO_2$ ratio within a range from 200 to 500.

The aluminates used are preferably the naturally occurring spinels, especially common spinel, zinc spinel, iron spinel or chromium spinel.

Preferred titanium dioxides are pure titanium dioxide in the rutile, anatase and brookite crystal forms, and also iron-containing titanium dioxides, for example ilmenite, calcium-containing titanium dioxides such as titanite or perovskite.

Preferred clay materials are those disclosed as clay materials in Hollemann and Wiberg, Lehrbuch der Anorganischen Chemie, Walter de Gruyter-Verlag, $91^{st}$-$100^{th}$ edition, 1985, on pages 783 to 785. Particularly the aforementioned section of this textbook is hereby incorporated by reference and is considered to form part of the disclosure of the present invention. Particularly preferred clay materials are kaolinite, illite, halloysite, montmorillonite and talc.

Further inorganic fines preferred in accordance with the invention are the metal salts of the mono-, oligo- and polyphosphoric acids. Among these, preference is given especially to the hydrates, particular preference being given to the mono- to decahydrates and trihydrates. Useful metals include especially alkali metals and alkaline earth metals, preference being given to the alkaline earth metals. Among these Mg and Ca are preferred and Mg is particularly preferred. In the context of phosphates, phosphoric acids and metal compounds thereof, reference is made to Hollemann and Wiberg, Lehrbuch der Anorganischen Chemie, Walter de Gruyter-Verlag, $91^{st}$-$100^{th}$ edition, 1985, on pages 651 to 669. The aforementioned section of this textbook is hereby incorporated by reference and is considered to form part of the disclosure of the present invention.

Preferred carbonaceous but nonorganic assistants are those pure carbons which are mentioned as graphites in Hollemann and Wiberg, Lehrbuch der Anorganischen Chemie, Walter de Gruyter-Verlag, $91^{st}$-$100^{th}$ edition, 1985, on pages 705 to 708. The aforementioned section of this textbook is hereby incorporated by reference and is considered to form part of the disclosure of the present invention. Particularly preferred graphites are synthetic graphites, for example coke, pyrographite, activated carbon or carbon black.

The superabsorbent particles used in the process according to the invention are preferably obtainable by first preparing a water-absorbing polymer (P) in particulate form from the aforementioned monomers and crosslinkers. This polymer (P) which serves as a starting material for the superabsorbent particles is produced, for example, by bulk polymerization which is preferably effected in kneading reactors such as extruders, solution polymerization, spray polymerization, inverse emulsion polymerization or inverse suspension polymerization. Preference is given to performing the solution polymerization in water as a solvent. The solution polymerization can be effected continuously or batchwise. The prior art discloses a wide spectrum of possible variations with regard to reaction conditions, such as temperatures, type and amount of the initiators, and of the reaction solution. Typical processes are described in the following patents: U.S. Pat. No. 4,286,082, DE 27 06 135, U.S. Pat. No. 4,076,663, DE 35 03 458, DE 40 20 780, DE 42 44 548, DE 43 23 001, DE 43 33 056, DE 44 18 818. The disclosures are hereby incorporated by reference and therefore form part of the disclosure.

The initiators used to initiate the polymerization may be all initiators which form free radicals under the polymerization conditions and are typically used in the production of superabsorbents. These include thermal catalysts, redox catalysts and photoinitiators, which are activated by means of high-energy radiation. The polymerization initiators may be present dissolved or dispersed in a solution of inventive monomers. Preference is given to the use of water-soluble catalysts.

Useful thermal initiators include all compounds which decompose to free radicals under thermal action and are known to those skilled in the art. Particular preference is given to thermal polymerization initiators having a half-life of less than 10 seconds, further preferably of less than 5 seconds at less than 180° C., further preferably at less than 140° C. Peroxides, hydroperoxides, hydrogen peroxide, persulphates and azo compounds are particularly preferred thermal polymerization initiators. In some cases, it is advantageous to use mixtures of different thermal polymerization initiators. Among these mixtures, preference is given to those of hydrogen peroxide and sodium peroxodisulphate or potassium peroxodisulphate, which can be used in any conceivable ratio. Suitable organic peroxides are preferably acetylacetone peroxide, methyl ethyl ketone peroxide, benzoyl peroxide, lauroyl peroxide, acetyl peroxide, capryl peroxide, isopropyl peroxydicarbonate, 2-ethylhexyl peroxydicarbonate, t-butyl hydroperoxide, cumene hydroperoxide, t-amyl perpivalate, t-butyl perpivalate, t-butyl perneohexanoate, t-butyl isobutyrate, t-butyl per-2-ethylhexanoate, t-butyl perisononanoate, t-butyl permaleate, t-butyl perbenzoate, t-butyl 3,5,5-trimethylhexanoate and amyl perneodecanoate. Further preferred thermal polymerization initiators are: azo compounds such as azobisisobutyronitrile, azobisdimethylvaleronitrile, 2,2'-azobis-(2-amidinopropane) dihydrochloride, azobisamidinopropane dihydrochlorde, 2,2'-azobis(N,N-dimethylene)isobutyramidine dihydrochloride, 2-(carbamoylazo)isobutyronitrile and 4,4'-azobis(4-cyanovaleric acid). The compounds mentioned are used in customary amounts, preferably within a range from 0.01 to 5 mol %, preferably from 0.1 to 2 mol %, based in each case on the amount of the monomers to be polymerized.

The redox catalysts comprise, as the oxidic component, at least one of the above-specified per compounds, and, as the reducing component, preferably ascorbic acid, glucose, sorbose, mannose, ammonium hydrogensulphite, sulphate, thiosulphate, hyposulphite or sulphide, alkali metal hydrogensulphite, sulphate, thiosulphate, hyposulphite or sulphide, metal salts such as iron(II) ions or silver ions, or sodium hydroxymethylsulphoxylate. The reducing component used in the redox catalyst is preferably ascorbic acid or sodium pyrosulphite. Based on the amount of monomers used in the polymerization, $1 \times 10^{-5}$ to 1 mol % of the reducing component of the redox catalyst and $1 \times 10^{-5}$ to 5 mol % of the oxidizing component of the redox catalyst are used. Instead of the oxidizing component of the redox catalyst, or in addition thereto, it is possible to use one or more, preferably water-soluble, azo compounds.

If the polymerization is triggered by the action of high-energy radiation, it is customary to use what are called photoinitiators as the initiator. These may be, for example, what are called α-splitters, H-abstracting systems, or else azides. Examples of such initiators are benzophenone derivatives such as Michler's ketone, phenanthrene derivatives, fluorene derivatives, anthraquinone derivatives, thioxanthone derivatives, coumarin derivatives, benzoin ethers and derivatives thereof, azo compounds such as the above-mentioned free-radical initiators, substituted hexaarylbisimidazoles or acylphosphine oxides. Examples of azides are: 2-(N,N-dimethylamino)ethyl 4-azidocinnamate, 2-(N,N-dimethylamino)ethyl 4-azidonaphthyl ketone, 2-(N,N-dimethylamino)ethyl 4-azidobenzoate, 5-azido-1-naphthyl 2'-(N,N-dimethylamino)ethyl sulphone, N-(4-sulphonylazidophenyl)maleimide, N-acetyl-4-sulphonylazidoaniline, 4-sulphonylazidoaniline, 4-azidoaniline, 4-azidophenacyl bromide, p-azidobenzoic acid, 2,6-bis(p-azidobenzylidene)cyclohexanone and 2,6-bis(p-azido-benzylidene)-4-methylcyclohexanone. The photoinitiators are, if they are used, employed typically in amounts of 0.01 to 5% by weight, based on the monomers to be polymerized.

Preference is given in accordance with the invention to using a redox system consisting of hydrogen peroxide, sodium peroxodisulphate and ascorbic acid. In general, the polymerization is initiated with the initiators within a temperature range from 0° C. to 90° C.

The polymerization reaction can be triggered by one initiator or by a plurality of interacting initiators. In addition, the polymerization can be performed in such a way that one or more redox initiators are first added. Later in the polymerization, thermal initiators or photoinitiators are then applied additionally, and the polymerization reaction in the case of photoinitiators is then initiated by the action of high-energy radiation. The reverse sequence, i.e. the initial initiation of the reaction by means of high-energy radiation and photoinitiators or thermal initiators and initiation of the polymerization by means of one or more redox initiators later in the polymerization, is also conceivable.

In order to convert the polymers (P) thus obtained to a particulate form, they can first, after they have been removed from the reaction mixture, be dried at a temperature within a range from 20 to 300° C., preferably within a range from 50 to 250° C. and more preferably within a range from 100 to 200° C., down to a water content of less than 40% by weight, preferably of less than 20% by weight and further preferably of less than 10% by weight, based in each case on the total weight of the polymer (P). The drying is effected preferably in ovens or driers known to those skilled in the art, for example in belt driers, staged driers, rotary tube ovens, fluidized bed driers, pan driers, paddle driers or infrared driers.

According to the present invention, the comminution is preferably effected by dry grinding, preferably by dry grinding in a hammer mill, a pinned disc mill, a ball mill or a roll mill.

In a preferred embodiment of the process according to the invention, the superabsorbent particles used are particles which have an inner region and a surface region bordering the inner region, the surface region having a different chemical composition from the inner region or differing from the inner region in a physical property. Physical properties in which the inner region differs from the surface region are, for example, the charge density or the degree of crosslinking.

These superabsorbent particles which have an inner region and a surface region bordering the inner region are preferably obtainable by postcrosslinking reactive groups close to the surface of the superabsorbent particles before or after they have been removed from the remaining particles of the particulate polymer (P). This postcrosslinking can be effected thermally, photochemically or chemically.

Preferred postcrosslinkers are the compounds of crosslinker classes II and IV mentioned in connection with the crosslinkers (α3).

Among these compounds, particularly preferred postcrosslinkers are diethylene glycol, triethylene glycol, polyethylene glycol, glycerol, polyglycerol, propylene glycol, diethanolamine, triethanolamine, polyoxypropylene, oxyethylene-oxypropylene block copolymers, sorbitan fatty acid esters, polyoxyethylenesorbitan fatty acid esters, trimethylolpropane, pentaerythritol, polyvinyl alcohol, sorbitol, 1,3-dioxolan-2-one (ethylene carbonate), 4-methyl-1,3-dioxolan-2-one (propylene carbonate), 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one, 1,3-dioxolan-2-one, poly-1,3-dioxolan-2-one.

Particular preference is given to using ethylene carbonate as the postcrosslinker.

Preferred embodiments of the superabsorbent particles are those which are postcrosslinked by crosslinkers of the following crosslinker classes or by crosslinkers of the following combinations of crosslinker classes: II, IV and II IV.

The crosslinker is preferably used in an amount within a range from 0.01 to 30% by weight, more preferably in an amount within a range from 0.1 to 20% by weight and further preferably in an amount within a range from 0.3 to 5% by weight, based in each case on the weight of the superabsorbent polymers in the postcrosslinking.

It is likewise preferred that the postcrosslinking is effected by contacting a fluid F comprising a solvent, preferably water, water-miscible organic solvents, for example methanol or ethanol or mixtures of at least two thereof, and the postcrosslinker with the outer region of the polymer particles at a temperature within a range from 30 to 300° C., more preferably within a range from 100 to 200° C. The contacting is preferably effected by spraying the fluid F onto the polymer particles and then mixing the polymer particles contacted with the fluid F. The postcrosslinker is present in the fluid F preferably in an amount within a range from 0.01 to 20% by weight, more preferably in an amount within a range from 0.1 to 10% by weight, based on the total weight of the fluid F. It is additionally preferred that the fluid F is contacted with the polymer particles in an amount within a range from 0.01 to 50% by weight, more preferably in an amount within a range from 0.1 to 30% by weight, based in each case on the weight of the polymer particles.

The fluid used in process step (vi) in the processes according to the invention preferably comprises a solvent and the crosslinkable, uncrosslinked polymer. The solvents used are preferably water or polar, water-miscible solvents such as acetone, methanol, ethanol, 2-propanol or mixtures of at least two thereof. The uncrosslinked polymer may be dissolved or dispersed in the solvent.

Useful condensation reactions preferably include the formation of ester, amide, imide or urethane bonds, preference being given to the formation of ester bonds. These ester bonds are preferably formed by the reaction of an OH group of the crosslinkable, uncrosslinked polymer with an acid group of the superabsorbent particle or with an acid group of the crosslinkable, uncrosslinked polymer.

The monomers (β1) containing acid groups are preferably neutralized to an extent of at least 10 mol %, more preferably to an extent of at least 20 mol %, further preferably to an extent of at least 40 mol % and even further preferably in the range from 45 to 80 mol %. The monomers can be neutralized before, during or only after the preparation of the crosslinkable, uncrosslinked polymer. The neutralization is preferably effected with the same bases which have already been mentioned in connection with the neutralization of the monomers (α1) bearing acid groups. In addition to the bases mentioned there, the uncrosslinked polymers are preferably also neutralized using bases which contain ammonium, calcium or magnesium as cations. Bases preferred in this context are ammonium carbonate, ammonia, calcium carbonate, calcium hydroxide, magnesium hydroxide and magnesium carbonate.

The monomers (β1) and (β2) used are preferably those monomers which are also used as preferred monomers (α1) and (α2) respectively.

In principle, useful monomers (M) or (β3) are all monomers suitable to the person skilled in the art, especially those of crosslinker class III. Preferred monomers (β3) are the reaction products of saturated aliphatic, cycloaliphatic, aromatic alcohols, amines or thiols with ethylenically unsaturated carboxylic acids, reactive carboxylic acid derivatives or allyl halides. Examples in this context include: (meth)allyl alcohol, (meth)allylamine, hydroxyl- or amino-containing esters of (meth)acrylic acid, such as hydroxyalkyl acrylates, especially hydroxymethyl (meth)acrylate, 2-hydroxyethyl (meth)acrylate or 2-hydroxypropyl (meth)acrylate, aminoalkyl (meth)acrylates, especially aminomethyl (meth)acrylate, 2-aminoethyl (meth)acrylate or 2-aminopropyl (meth)acrylate, mono(meth)allyl compounds of polyols, preferably of diols, for example polyethylene glycols or polypropylene glycols, and glycidylalkyl (meth)acrylates such as glycidyl (meth)acrylate.

Particularly preferred crosslinkable, uncrosslinked polymers which are used in the processes according to the invention are those polymers based on 1 to 80% by weight, more preferably on 1 to 60% by weight and further preferably on 1 to 20% by weight of (meth)acrylamide and 20 to 99% by weight, more preferably on 40 to 99% by weight and further preferably on 80 to 99% by weight, based in each case on the total weight of the uncrosslinked polymer, on (meth)acrylic acid, the (meth)acrylic acid being preferably partly neutralized.

It is additionally preferred that the fluid used in the process according to the invention, in addition to the solvent and the crosslinkable, uncrosslinked polymer, comprises a further external crosslinker. This is especially true when the crosslinkable, uncrosslinked polymers do not include any monomers (M) or (β3). Preferred further external crosslinkers are those of crosslinker classes II and IV which have already been mentioned in connection with the crosslinkers (α3). Particularly preferred further crosslinkers are those which have been mentioned as particularly preferred crosslinkers of classes II and IV in connection with the monomers (α3). It is further preferred in this context that the fluid comprises the further external crosslinker in an amount within a range from 0.01 to 30% by weight, preferably within a range from 0.1 to 15% by weight and more preferably within a range from 0.2 to 7% by weight, based on the weight of the uncrosslinked polymer.

Preferred additives are substances which reduce the brittleness of the superabsorbent particles produced by the process according to the invention, for instance polyethylene glycol, polypropylene glycol, mixed polyalkoxylates, polyalkoxylates based on polyols such as glycerol, trimethylolpropane or butanediol, surfactants with an HLB of more than 10, such as alkyl polyglucosides or ethoxylated sugar esters, for example polysorbates under the Tween trade name from ICI. Some of these additives also act simultaneously as further crosslinkers, for example polyethylene glycol, polypropylene glycol, trimethylolpropane or butanediol.

Further preferred additives are agents which reduce the hardness of the superabsorbent particles produced by the process according to the invention, for example cationic surfactants such as alkyltrimethylammonium chloride, dialkyldimethylammonium chloride, dimethylstearylammonium chloride, alkylbenzyldimethylammonium chloride, or the corresponding methylsulphates, quaternary tall oil fatty acid imidazolinium methosulphates. These additives are preferably used in amounts within a range from 0 to 5% by weight, more preferably within a range from 0.5 to 4% by weight, based on the weight of the uncrosslinked polymer. The additives can be added either before or after the polymerization. They bind the polycarboxylates by anion-cation interaction and thus bring about the softening effect. They simultaneously bring about an improvement in the absorption capacity for aqueous liquids. Another advantage of the substances is the biocidal action thereof, which prevents unwanted degradation of the swelling agents. This property is particularly important for some applications.

Preferred additives are additionally release agents, for instance inorganic or organic pulverulent release agents. These release agents are preferably used in amounts within a range from 0 to 2% by weight, more preferably within a range from 0.1 to 1.5% by weight, based on the weight of the crosslinked polymer. Preferred release agents are wood flour, pulp fibres, powdered bark, cellulose powder, mineral fillers such as perlite, synthetic fillers such as nylon powder, rayon powder, diatomaceous earth, bentonite, kaolin, zeolites, talc, loam, ash, carbon dust, magnesium silicates, fertilizers or mixtures of the substances. Finely divided fumed silica, as sold under the Aerosil trade name by Evonik Degussa, is preferred.

In a preferred embodiment of the process according to the invention, the superabsorbent particles are contacted with the fluid comprising the uncrosslinked polymer in the presence of an effect substance based on a polysugar or a compound containing silicon-oxygen or a mixture of at least two thereof. The effect substance may be present in the fluid or else may be mixed with the superabsorbent particles before the contacting of the superabsorbent particles with the fluid. It is also possible that the effect substance is dissolved or dispersed in a further fluid F' and is contacted with the superabsorbent particles in the form of this solution or dispersion together with the fluid. The fluid F' comprises, in addition to the effect substance, preferably a liquid, particularly preferred liquids being water and organic solvents, for example methanol or ethanol, or else mixtures of at least two thereof, particular preference being given to water as the liquid.

Useful polysugars in accordance with the invention include all starches familiar to the person skilled in the art and derivatives thereof, and also celluloses and derivatives thereof, and cyclodextrins, the cyclodextrins used being preferably α-cyclodextrin, β-cyclodextrin, γ-cyclodextrin or mixtures of these cyclodextrins.

Preferred compounds containing silicon-oxygen are zeolites. The zeolites used may be all synthetic or natural zeolites known to those skilled in the art. Preferred natural zeolites are zeolites from the natrolite group, the harmotone group, the mordenite group, the chabasite group, the faujasite group (sodalite group) or the analcite group. Examples of natural zeolites are analcime, leucite, pollucite, wairakite, bellbergite, bikitaite, boggsite, brewsterite, chabazite, willhendersonite, cowlesite, dachiardite, edingtonite, epistilbite, erionite, faujasite, ferrierite, amicite, garronite, gismondine, gobbinsite, gmelinite, gonnardite, goosecreekite, harmotome, phillipsite, wellsite, clinoptilolite, heulandite, laumontite, levyne, mazzite, merlinoite, montesommaite, mordenite, mesolite, natrolite, scolecite, offretite, paranatrolite, paulingite, perlialite, barrerite, stilbite, stellerite, thomsonite, tschernichite or yugawaralite. Preferred synthetic zeolites are zeolite A, zeolite X, zeolite Y, zeolite P, or the product ABSCENTS.

The cations present in the zeolites used in the process according to the invention are preferably alkali metal cations such as $Li^+$, $Na^+$, $K^+$, $Rb^+$, $Cs^+$ or $Fr^+$ and/or alkaline earth metal cations such as $Mg^{2+}$, $Ca^{2+}$, $Sr^{2+}$ or $Ba^{2+}$.

The zeolites used may be zeolites of what is called the "intermediate" type, in which the $SiO_2/AlO_2$ ratio is less than 10; the $SiO_2/AlO_2$ ratio of these zeolites is more preferably within a range from 2 to 10. In addition to these "intermediate" zeolites, it is also possible to use zeolites of the "high" type, which include, for example, the known "molecular sieve" zeolites of the ZSM type, and beta-zeolite. These "high" zeolites are preferably characterized by an $SiO_2/AlO_2$ ratio of at least 35, more preferably by an $SiO_2/AlO_2$ ratio within a range from 200 to 500.

The zeolites are preferably used in the form of particles with a mean particle size within a range from 1 to 500 μm, more preferably within a range from 2 to 200 μm and further preferably within a range from 5 to 100 μm.

The effect substances are used in the processes according to the invention preferably in an amount within a range from 0.1 to 50% by weight, more preferably within a range from 1 to 40% by weight and further preferably in an amount within a range from 5 to 30% by weight, based in each case on the weight of the superabsorbent particles.

Preferred microbe-inhibiting substances are in principle all substances active against Gram-positive bacteria, for example 4-hydroxybenzoic acid and salts and esters thereof, N-(4-chlorophenyl)-N'-(3,4-dichlorophenyl)urea, 2,4,4'-trichloro-2'-hydroxydiphenyl ether (triclosan), 4-chloro-3,5-dimethylphenol, 2,2'-methylenebis(6-bromo-4-chlorophenol), 3-methyl-4-(1-methylethyl)phenol, 2-benzyl-4-chlorophenol, 3-(4-chlorophenoxy)-1,2-propanediol, 3-iodo-2-propynyl butylcarbamate, chlorhexidine, 3,4,4'-trichlorocarbonilide (TTC), antibacterial fragrances, thymol, thyme oil, eugenol, clove oil, menthol, mint oil, farnesol, phenoxyethanol, glyceryl monocaprinate, glyceryl monocaprylate, glyceryl monolaurate (GML), diglyceryl monocaprinate (DMC), N-alkylsalicylamides, for example N-octylsalicylamide or N-decylsalicylamide.

Suitable enzyme inhibitors are, for example, esterase inhibitors. These are preferably trialkyl citrates such as trimethyl citrate, tripropyl citrate, triisopropyl citrate, tributyl citrate and especially triethyl citrate (Hydagen TM CAT, Cognis GmbH, Dusseldorf, Germany). The substances inhibit enzyme activity and as a result reduce odour formation. Further substances useful as esterase inhibitors are sterol sulphates or phosphates, for example lanosterol sulphate or phosphate, cholesterol sulphate or phosphate, campesterol sulphate or phosphate, stigmasterol sulphate or phosphate and sitosterol sulphate or phosphate, dicarboxylic acids and esters thereof, for example glutaric acid, monoethyl glutarate, diethyl glutarate, adipic acid, monoethyl adipate, diethyl adipate, malonic acid and diethyl malonate, hydroxycarboxylic acids and esters thereof, for example citric acid, malic acid, tartaric acid or diethyl tartrate, and zinc glycinate.

Suitable odour absorbers are substances which can adsorb and substantially retain odour-forming substances. They lower the partial pressure of the individual components and thus also reduce the rate of spread thereof It is important that perfumes must remain unimpaired. Odour absorbers have no effect against bacteria. They contain, for example, as the main constituent, a complex zinc salt of ricinoleic acid or specific, substantially odour-neutral fragrances known to the person skilled in the art as "fixatives", for example extracts of labdanum or styrax or particular abietic acid derivatives. The function of odour maskers is fulfilled by odorants or perfume oils which, in addition to their function as odour maskers, impart their particular fragrance notes to the deodorants. Examples of perfume oils include mixtures of natural and synthetic odorants. Natural odorants are extracts of flowers, stems and leaves, fruits, fruit skins, roots, woods, herbs and grasses, needles and twigs, and also resins and balsams. Additionally useful are animal raw materials, for example civet and castoreum. Typical synthetic odorant compounds are products of the ester, ether, aldehyde, ketone, alcohol and hydrocarbon type. Odorant compounds of the ester type are, for example, benzyl acetate, p-tert-butylcyclohexyl acetate, linalyl acetate, phenylethyl acetate, linalyl benzoate, benzyl formate, allylcyclohexyl propionate, styrallyl propionate and benzyl salicylate. The ethers include, for example, benzyl ethyl ether; the aldehydes include, for example, the linear alkanals having 8 to 18 carbon atoms, citral, citronellal, citronellyloxyacetaldehyde, cyclamen aldehyde, hydroxycitronellal, lilial and bourgeonal; the ketones include, for example, the ionones and methyl cedryl ketone; the alcohols include anethole, citronellol, eugenol, isoeugenol, geraniol, linalool, phenylethyl alcohol and terpineol; the hydrocarbons include principally the terpenes and balsams. Preference is given, however, to using mixtures of different odorants which together produce a pleasing fragrance note. Suitable perfume oils are also essential oils of relatively low volatility which are usually used as aroma components, for example sage oil, camomile oil, clove oil, melissa oil, mint oil, cinnamon leaf oil, lime blossom oil, juniperberry oil, vetiver oil, olibanum oil, galbanum oil, labdanum oil and lavender oil. Preference is given to using bergamot oil, dihydromyrcenol, lilial, lyral, citronellol, phenylethyl alcohol, alpha-hexylcinnamaldehyde, geraniol, benzylacetone, cyclamen aldehyde, linalool, Boisambrene Forte, ambroxan, indole, Hedione, Sandelice, lemon oil, mandarin oil, orange oil, allyl amyl glycolate, cyclovertal, lavender oil, clary sage oil, beta-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, Romilat, Irotyl and Floramat, alone or in mixtures.

Antiperspirants reduce the formation of perspiration by influencing the activity of the eccrine sweat glands, and thus counteract underarm wetness and body odour. Suitable astringent active antiperspirant ingredients are in particular salts of aluminium, zirconium or zinc. Such suitable antihydrotically active ingredients are, for example, aluminium chloride, aluminium chlorohydrate, aluminium dichlorohydrate, aluminium sesquichlorohydrate and the complexes thereof, for example with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and the complexes thereof, for example with amino acids such as glycine.

Suitable apparatuses for mixing or spraying are all of those which allow homogeneous distribution of the fluid on or with the superabsorbent particles. Examples are Lodige mixers (manufactured by Gebrüder Lödige Maschinenbau GmbH), Gericke multi-flux mixers (manufactured by Gericke GmbH), DRAIS mixers (manufactured by DRAIS GmbH Spezialmaschinenfabrik Mannheim), Hosokawa mixers (Hosokawa Mokron Co., Ltd.), Ruberg mixers (manufactured by Gebr. Ruberg GmbH & Co. KG Nieheim), Hüttlin coaters (manufactured by BWI Hüttlin GmbH Steinen), fluidized bed driers or spray granulators from AMMAG (manufactured by AMMAG Gunskirchen, Austria) or Heinen (manufactured by A. Heinen AG Anlagenbau Varel), Patterson-Kelly mixers, NARA paddle mixers, screw mixers, pan mixers, fluidized bed driers, Schugi mixers or PROCESSALL.

For contacting in a fluidized bed, it is possible to employ all fluidized bed processes which are known to those skilled in the art and appear to be suitable. For example, it is possible to use a fluidized bed coater.

A further to the achievement of the objects described at the outset is made by a composite including the inventive superabsorbents or the superabsorbents obtainable by the process according to the invention and a substrate. It is preferable that the inventive superabsorbents and the substrate are bonded in a fixed manner to one another. Preferred substrates are films of polymers, for example of polyethylene, polypropylene or polyamide, metals, nonwovens, fluff, tissues, fabrics, natural or synthetic fibres, or other foams. It is additionally preferred in accordance with the invention that the composite comprises at least one region which includes the inventive superabsorbent in an amount in the range from about 15 to 100% by weight, preferably about 30 to 100% by weight, more preferably from about 50 to 99.99% by weight, further preferably from about 60 to 99.99% by weight and even further preferably from about 70 to 99% by weight, based in each case on the total weight of the region of the composite in question, this region preferably having a size of at least 0.01 $cm^3$, preferably at least 0.1 $cm^3$ and most preferably at least 0.5 $cm^3$.

A particularly preferred embodiment of the inventive composite involves a flat composite as described in WO 02/056812 A1 as an "absorbent material". The disclosure-content of WO 02/056812 A1, especially with regard to the exact structure of the composite, the basis weight of the constituents thereof and the thickness thereof, is hereby incorporated by reference and forms part of the disclosure of the present invention.

A further contribution to the achievement of at least one of the objects stated at the outset is made by a process for producing a composite, wherein the inventive water-absorbing polymers or the superabsorbents obtainable by the process according to the invention and a substrate and optionally an additive are contacted with one another. The substrates used are preferably those substrates which have already been mentioned above in connection with the inventive composite.

A contribution to the achievement of at least one of the objects stated at the outset is also made by a composite obtainable by the process described above, this composite preferably having the same properties as the above-described inventive composite.

A further contribution to the achievement of at least one of the objects stated at the outset is made by chemical products including the inventive superabsorbents or an inventive composite. Preferred chemical products are especially foams, mouldings, fibres, foils, films, cables, sealing materials, liquid-absorbing hygiene articles, especially nappies and sanitary towels, carriers for plant growth or fungal growth regulators or plant protection active ingredients, additives for building materials, packaging materials or soil additives.

The use of the inventive superabsorbents or of the inventive composite in chemical products, preferably in the aforementioned chemical products, especially in hygiene articles such as nappies or sanitary towels, and the use of the superabsorbent particles as carriers for plant growth or fungal growth regulators or plant protection active ingredients make a contribution to the achievement of at least one of the objects stated at the outset. In the case of use as a carrier for plant growth or fungal growth regulators or plant protection active ingredients, it is preferred that the plant growth or fungal growth regulators or plant protection active ingredients can be released over a period controlled by the carrier.

Test Methods

Unless stated otherwise hereinafter, the measurements conducted herein are according to ERT methods. "ERT" stands for EDANA Recommended Test and "EDANA" for European Disposables and Nonwovens Association.

Centrifuge Retention Capacity (CRC)

The centrifuge retention capacity is determined by EDANA (European Disposables and Nonwovens Association) recommended test method No. 441.2-02 "Centrifuge retention capacity".

Determination of the Free Swell Rate (FSR)

The absorption rate was determined via the measurement of the Free Swell Rate (FSR) by the test method described in EP-A-0 443 627 on page 12.

Determination of Permeability

The permeability is determined by the measurement of the "Saline Flow Conductivity—SFC" by the test method described in WO-A-95/26209.

The examples which follow serve for further illustration of the invention, but without restricting it thereto.

EXAMPLE 1

A monomer solution consisting of 2480 g of acrylic acid, 3124 g of water, 14.92 g of polyethylene glycol-300 diacrylate, 11.94 g of monoallyl polyethylene glycol-450 monoacrylate is freed of dissolved oxygen by purging with nitrogen. The acrylic acid has been neutralized to an extent of 70 mol % with sodium hydroxide solution (in this example with 1927 g of 50% NaOH). The nitrogen purging is effected over a period of approx. 10 minutes. During the inert gas purging, 2.33 g of sodium peroxodisulphate in 50 g of water are added to the monomer solution. Shortly before transfer of the monomer solution to the polymerization reactor, 0.54 g of 35% hydrogen peroxide solution in 50 g of water is added to the monomer solution purged with inert gas. This is followed by the transfer of the monomer solution to the polymerization reactor, which is conducted in an inert gas countercurrent. The polymerization reactor consists of a twin-shaft corotatory batchwise kneading reactor (LIST 10 liters CKR kneading reactor). The reactor is kept at jacket temperature approx. 85° C. by means of jacket and shaft heating prior to addition of the monomer solution. The shafts of the reactor rotate at 30 revolutions per minute. Immediately after transfer of the monomer solution to the reactor, 0.5% by weight of sodium carbonate (produced in a fluidized bed spray granulation process, particle size 400-600 μm) is added to the monomer solution and distributed in the reaction space by the rotating shafts. This is followed by addition of 0.233 g of ascorbic acid in 50 g of water as a polymerization initiator. An exothermic polymerization reaction takes place. The adiabatic end temperature is in the range from 105° C. to 110° C. and the residence time of the reaction mixture is 10 minutes. Without further comminution steps, the resulting hydrogel is dried in a laboratory forced air drying cabinet at 150° C. for 120 minutes.

The dried polymer is comminuted in a Retsch cutting mill (2 mm). Sieving gives a particle size of the comminuted, dried superabsorbent of 150 μm to 850 μm.

| Process | CRC (g/g) | FSR (g/g/s) |
| --- | --- | --- |
| Example 1 | 30.8 | 0.35 |

Surface Postcrosslinking

A subsequent surface postcrosslinking is conducted with dried, ground and sieved polymer particles (=precursor material) from Example 1. For this purpose, the surface postcrosslinking solution consisting of Example 1a) ethylene carbonate/water (1 or 3% by weight based on superabsorbent mass) or Example 1b) ethylene carbonate/water/aluminium sulphate/aluminium lactate (1/3/0.3/0.4% by weight based on superabsorbent mass) is sprayed onto the precursor material by means of a disposable syringe and blended in a Krupps mixer. Drying/surface postcrosslinking is effected in a laboratory drying cabinet either at 170° C./90 minutes (i) or 180° C./30 minutes (ii). The following CRC and FSR values were measured:

| Process | CRC (g/g) | FSR (g/g/s) |
| --- | --- | --- |
| Example 1a)-i | 27.5 | 0.36 |
| Example 1.a)-ii | 28.5 | 0.31 |
| Example 1.b)-i | 26.4 | 0.29 |
| Example 1.b)-ii | 27.7 | 0.30 |

EXAMPLE 2

A monomer solution consisting of 2560 g of acrylic acid which has been neutralized to an extent of 70 mol % with sodium hydroxide solution (1989 g of 50% NaOH), 3363 g of water, 9.21 g of polyethylene glycol-300 diacrylate, 13.31 g of monoallyl polyethylene glycol-450 monoacrylate is made up. 2 kg of this are taken for a polymerization. The 2 kg of the monomer solution taken are freed of dissolved oxygen by purging with nitrogen. The nitrogen purging is performed for approx. 15 minutes. During the inert gas purging, 0.60 g of sodium peroxodisulphate in 10 g of water are added to the monomer solution. Shortly before transfer of the monomer solution to the polymerization reactor, 0.14 g of 35% hydrogen peroxide solution in 10 g of water is added to the monomer solution purged with inert gas. This is followed by the transfer of monomer solution to the polymerization reactor in an inert gas countercurrent. The polymerization reactor consists of a twin-shaft corotatory batchwise kneading reactor (LIST 2.5 liters CRP kneading reactor). Before addition of the monomer solution, the reactor is heated to jacket temperature approx. 75° C. by means of a jacket and the temperature is maintained. The shafts of the reactor are rotated at 60 revolutions per minute. Immediately after transfer of the monomer solution to the reactor, 0.5% by weight of sodium carbonate (produced in a fluidized bed spray granulation process, particle size 400-600 μm) is added to the monomer solution and distributed in the reaction space by the rotating shafts. Thereafter, 0.03 g of ascorbic acid in 2 g of water is added as a polymerization initiator. The target temperature of the thermostating of the heating circuit of the reactor jacket heating is set to 100° C. directly after the start of the reaction. An exothermic polymerization reaction takes place. The adiabatic end temperature is in the range from 105° C. to 110° C. The residence time of the reaction mixture is 10 minutes. Without further comminution steps, the hydrogel formed is dried in a laboratory forced air drying cabinet at 150° C. for 120 minutes.

The dried polymer is comminuted in a Retsch cutting mill (2 mm). Sieving gives a particle size of the comminuted dried superabsorbent of 150 μm to 850 μm.

| Process | CRC (g/g) | FSR (g/g/s) |
| --- | --- | --- |
| Example 2 | 32.4 | 0.34 |

Surface Postcrosslinking:

A subsequent surface postcrosslinking is conducted with dried, ground and sieved polymer particles (=precursor material) from Example 2. For this purpose, the surface postcrosslinking solution consisting of Example 2a) ethylene carbonate/water/aluminium sulphate/aluminium lactate (1/3/0.3/0.4% by weight based on superabsorbent mass) is sprayed onto the precursor material by means of a disposable syringe and blended in a Krupps mixer. This is then followed by drying/surface postcrosslinking in a laboratory drying cabinet either at 170° C./90 minutes (i) or 180° C./30 minutes (ii). The following FSR values were measured:

| Process | CRC (g/g) | FSR (g/g/s) |
| --- | --- | --- |
| Example 2a)-i | 29.1 | 0.35 |
| Example 2a)-ii | 28.9 | 0.34 |

EXAMPLE 3

A monomer solution consisting of 2560 g of acrylic acid which has been neutralized to an extent of 70 mol % with sodium hydroxide solution (1989 g of 50% NaOH), 3363 g of water, 9.21 g of polyethylene glycol-300 diacrylate, 13.31 g of monoallyl polyethylene glycol-450 monoacrylate is made up. 2 kg of this are taken for a polymerization. The 2 kg of the monomer solution taken are freed of dissolved oxygen by purging with nitrogen. The nitrogen purging is performed for approx. 15 minutes. During the inert gas purging, 0.60 g of sodium peroxodisulphate in 10 g of water are added to the monomer solution. Shortly before transfer of the monomer solution to the polymerization reactor, 0.14 g of 35% hydrogen peroxide solution in 10 g of water is added to the monomer solution purged with inert gas. Then the monomer solution is transferred to the polymerization reactor in an inert gas countercurrent. The polymerization reactor consists of a twin-shaft corotatory batchwise kneading reactor (LIST 2.5 liters CRP kneading reactor). Before addition of the monomer solution, the reactor is heated to jacket temperature approx. 75° C. by means of a jacket and the temperature is maintained. The shafts of the reactor are rotated at 60 revolutions per minute. Immediately after transfer of the monomer solution to the reactor, 1.0% by weight of sodium carbonate (produced in a fluidized bed spray granulation process, particle size 400-600 µm) is added to the monomer solution and distributed in the reaction space by the rotating shafts. Thereafter, 0.03 g of ascorbic acid in 2 g of water is added as a polymerization initiator. The target temperature of the thermostating of the heating circuit of the reactor jacket heating is set to 100° C. directly after the start of the reaction. An exothermic polymerization reaction takes place. The adiabatic end temperature is in the range from 105° C. to 110° C. The residence time of the reaction mixture is 10 minutes. Without further comminution steps, the hydrogel formed is dried in a laboratory forced air drying cabinet at 150° C. for 120 minutes. The dried polymer is subsequently comminuted in a Retsch cutting mill (2 mm). Sieving gives a particle size of the comminuted dried superabsorbent of 150-850 µm.

| Process | CRC (g/g) | FSR (g/g/s) |
|---|---|---|
| Example 3 | 33.1 | 0.38 |

Surface Postcrosslinking:

A subsequent surface postcrosslinking is conducted with dried, ground and sieved polymer particles (=precursor material) from Example 3. For this purpose, the surface postcrosslinking solution consisting of Example 3a) ethylene carbonate/water/aluminium sulphate/aluminium lactate (1/3/0.3/0.4% by weight based on superabsorbent mass) is sprayed onto the precursor material by means of a disposable syringe and blended in a Krupps mixer. This is then followed by drying/surface postcrosslinking in a laboratory drying cabinet either at 170° C./90 minutes (i) or 180° C./30 minutes (ii). The following CRC and FSR values were measured:

| Process | CRC (g/g) | FSR (g/g/s) |
|---|---|---|
| Example 3a)-i | 30.7 | 0.36 |
| Example 3a)-ii | 31.4 | 0.35 |

EXAMPLE 4

A monomer solution composed of NaOH and acrylic acid with a degree of neutralization of 70 mol % and an acrylic acid WS of 32% are prepared. In this monomer solution, 0.2% (based on acrylic acid) of polyethylene glycol-300 diacrylate crosslinker and 0.4% (based on acrylic acid) of monoallyl polyethylene glycol-450 monoacrylate as a crosslinker are dissolved. The monomer solution is purged with nitrogen in a 3 l beaker for 30 minutes in order to remove the dissolved oxygen. At a temperature of 4° C., 0.5% granulated soda (400-600 µm) is added and then the polymerization is started by the successive addition of 0.3 g of sodium peroxodisulphate in 10 g of dist. water, 0.07 g of 35% hydrogen peroxide solution in 10 g of distilled water and 0.015 g of ascorbic acid in 2 g of dist. water. Once the final temperature (about 100° C.) has been obtained, the gel is comminuted with a meat grinder and dried in a laboratory forced air drying cabinet at 150° C. for 2 h. The dried powder is coarsely crushed, ground and sieved off to a particle fraction of 150-850 µm.

| Process | CRC (g/g) | FSR (g/g/s) |
|---|---|---|
| Example 4 | 30.9 | 0.31 |

Surface Postcrosslinking:

A subsequent surface postcrosslinking is conducted with dried, ground and sieved polymer particles (=precursor material) from Example 4. For this purpose, the surface postcrosslinking solution consisting of Example 4a) ethylene carbonate/water/aluminium sulphate/aluminium lactate (1/3/0.3/0.4% by weight based on superabsorbent mass) is sprayed onto the precursor material by means of a disposable syringe and blended in a Krupps mixer. This is then followed by drying/surface postcrosslinking in a laboratory drying cabinet either at 170° C./90 minutes (i) or 180° C./30 minutes (ii). The following CRC and FSR values were measured:

| Process | CRC (g/g) | FSR (g/g/s) |
|---|---|---|
| Example 4a)-i | 26.9 | 0.26 |
| Example 4a)-ii | 27.5 | 0.27 |

In spite of the addition of the granulated sodium carbonate, there was no improvement in the FSR when a pot mixer was used.

EXAMPLE 5

The batch sizes and the experimental procedure including the postcrosslinking are in accordance with Examples 2 and 2a). The only difference is that the addition of the sodium carbonate (0.5% by weight) directly follows addition of the ascorbic acid.

| Process | CRC (g/g) | FSR (g/g/s) |
|---|---|---|
| Example 5, precursor | 35.2 | 0.38 |
| Example 5 a)-i | 31.3 | 0.29 |
| Example 5 a)-ii | 31.2 | 0.25 |

According to the invention, the time of addition affects the resulting FSR, and it should preferably follow $H_2O_2$ addition and precede ascorbic acid addition.

EXAMPLE 6

Comparative Example

The batch sizes and the experimental procedure including the postcrosslinking are in accordance with Example 2 and Example 2a). The experiment was conducted without the addition of sodium carbonate.

| Process | CRC (g/g) | FSR (g/g/s) |
|---|---|---|
| Example 6, precursor | 31.6 | 0.33 |
| Example 6a)-i | 28.4 | 0.23 |
| Example 6 a)-ii | 28.6 | 0.20 |

The comparative example shows that the FSR without the addition of sodium carbonate does not have an inventive increase after the postcrosslinking step.

What is claimed is:

1. A process for producing a water-absorbing polymer composition, comprising the process steps of
   (i) forming an aqueous monomer solution by mixing
      ($\alpha$1) from 0.1 to 99.999% by weight, of polymerizable, ethylenically unsaturated monomers containing acid groups or salts thereof or polymerizable, ethylenically unsaturated monomers including a protonated or quaternized nitrogen, or mixtures thereof,
      ($\alpha$2) from 0 to 70% by weight of polymerizable, ethylenically unsaturated monomers copolymerizable with ($\alpha$1),
      ($\alpha$3) from 0.001 to 10% by weight of one or more crosslinkers,
      ($\alpha$4) from 0 to 30% by weight of water-soluble polymers, and
      ($\alpha$5) from 0 to 20% by weight of one or more assistants, where the sum of their weights ($\alpha$1) to ($\alpha$5) is 100% by weight,
   (ii) free-radical polymerization with crosslinking to form a water-insoluble aqueous untreated hydrogel polymer,
   (iii) drying the hydrogel polymer,
   (iv) grinding and sieving the water-absorbing polymer,
   (v) surface postcrosslinking the ground hydrogel polymer of step (iv), and
   (vi) drying and finishing the water-absorbing polymer,
   wherein the process in steps i) and ii) is done in a kneading reactor having at least one shaft and not through a reactor employing a poly belt, and wherein granulated blowing agents consisting of soda carbonate particles having a particle size of 100 µm to 900 µm are added to the aqueous monomer solution of part (i) prior to the addition of an initiator and the start of the free-radical polymerization, and wherein the water-absorbing polymer composition has a FSR is in the range from 0.4 to 0.55.

2. The process according to claim 1, wherein iii), a comminution the water-insoluble aqueous untreated hydrogel polymer prior to the drying of the hydrogel polymer.

3. The process according to claim 1 wherein the blowing agents have a preferred particle size of 200 µm to 800 µm.

4. The process according to claim 1, wherein the blowing agent consist of soda carbonate particles having a layer structure.

5. The process according to claim 1 wherein the process steps i) and ii) are effected batchwise or continuously in the kneading reactor.

6. The process according to claim 1 wherein the process steps i) and ii) according to claim 1 are done batchwise in the kneading reactor.

7. The process according to claim 5 wherein the kneading reactor is operated batchwise or continuously with an at least one-shaft system and the granulated blowing agent is incorporated homogeneously in the in the aqueous monomer solution.

* * * * *